United States Patent [19]

Feitler et al.

[11] Patent Number: 5,013,843

[45] Date of Patent: May 7, 1991

[54] HIGH YIELD OF PYRIDINE AND/OR ALKYLPYRIDINE(S) IN CONDENSATION REACTION OF TERNARY ALDEHYDES AND/OR KETONES WITH AMMONIA

[75] Inventors: David Feitler, New Windsor; Henry Wetstein, Monroe, both of N.Y.

[73] Assignee: Nepera, Inc., Harriman, N.Y.

[21] Appl. No.: 535,239

[22] Filed: Jun. 7, 1990

[51] Int. Cl.$^5$ .................. C07D 213/8; C07D 213/9; C07D 213/10

[52] U.S. Cl. .................................. 546/251; 546/250

[58] Field of Search ............................. 546/250, 257

[56] References Cited

U.S. PATENT DOCUMENTS

| | | | |
|---|---|---|---|
| 3,946,020 | 3/1976 | Minato et al. | 502/263 |
| 4,220,783 | 9/1980 | Chang et al. | 546/251 |
| 4,675,410 | 6/1987 | Feitler et al. | 546/251 |

FOREIGN PATENT DOCUMENTS

| | | | |
|---|---|---|---|
| 232182 | 2/1987 | European Pat. Off. | 546/251 |
| 45-39262 | 6/1967 | Japan | 546/251 |
| 61-53265 | 8/1984 | Japan | 546/251 |
| 61-53266 | 8/1984 | Japan | 546/251 |
| 929694 | 7/1963 | United Kingdom | 546/251 |
| 966264 | 8/1964 | United Kingdom | 546/251 |
| 1141526 | 1/1969 | United Kingdom | 546/251 |

OTHER PUBLICATIONS

"Pyridine and Pyridine Derivatives", Goe, Kirk-Othmer, vol. 19, 454–483 (1982).

Golunski et al., Applied Catalysis, 23 (1986), 1–14.

*Primary Examiner*—Alan L. Rotman
*Attorney, Agent, or Firm*—Millen, White & Zelano

[57] ABSTRACT

A third aldehyde or ketone is added to a binary mixture of aldehyde and/or ketones used in preparing mixtures of pyridine and alkyl-substituted pyridines in large scale continuous processes. The amount of the third component is appropriately adjusted whereby the relative ratio(s) of products are adjusted and the total yield of pyridines and/or alkyl-substituted pyridines is high, all without any plant shut-down. In a preferred system, propionaldehyde is added to a binary mixture of acetaldehyde and formaldehyde to produce surprisingly high amounts of beta-pyridine and pyridine.

17 Claims, No Drawings

5,013,843

HIGH YIELD OF PYRIDINE AND/OR ALKYLPYRIDINE(S) IN CONDENSATION REACTION OF TERNARY ALDEHYDES AND/OR KETONES WITH AMMONIA

This application is a continuation-in-part of application Ser. No. 263,754 filed Oct. 28, 1988.

BACKGROUND OF THE INVENTION

This invention relates to an improved large scale process for reacting aldehydes and/or ketones with ammonia over an effective zeolitic catalyst to form a mixture of pyridine and/or alkylpyridine(s).

The condensation reaction is well known whereby carbonyl-containing compounds can be reacted with ammonia to form pyridine-type bases, including pyridine and alkylpyridines such as the picolines (alpha, beta and gamma), the lutidines, ethylpyridines, etc., using an amorphous or a zeolitic catalyst. Depending on the choice of aldehydes and/or ketones, the major product can be varied and is determined primarily by the underlying stoichiometry of the reaction, statistical considerations and in the case of zeolitic catalysis by pore size considerations.

However, the product mixture in all cases is a complicated blend of pyridine and the alkylpyridines. Methods have long been sought to improve the controllability of the underlying reaction whereby the relative ratios of products can be better and more easily selected, preferably without loss of total yield. This is especially critical in the case of large scale, continuous systems, e.g., of the pilot plant or full commercial production scale, where it is imperative that any technique for adjusting product composition be implementable without highly expensive and inefficient system shut-down. Very few such techniques exist.

Such ease of controllability would provide a major advantage since the marketplace demand for each product fluctuates periodically. Historically, pyridine has been the major product in view of its use as an intermediate for other industrial products. See, e.g., "Pyridine and Pyridine Derivatives", Goe, Kirk-Othmer, Volume 19, 454-483 (1982), and Golunski et al., *Applied Catalysis*, 23 (1986), 1-14. However, in recent times, the market has undergone more dramatic changes whereby the relative demand for alkylpyridines has increased, especially for beta-pyridine, e.g., as an intermediate for preparation of niacinamide and other medicinal, agricultural and chemical products. Thus, it is presently especially valuable to have facile, on-line methods for varying the relative yields of pyridine and the various alkylpyridines in a given reaction, without significant loss of total yield. On a commercial scale, losses of even one percent will have major economic repercussions.

Various factors have been noted in the past which affect product composition and yield in one way or another. For example, Grigolet (German Patent 20 51 316) describes the effect of coke levels on the product of the reaction of crotonaldehyde using an amorphous catalyst. The desire is to minimize betapicoline production. On the other hand, Uebel et al. [Chem. Tech. (Leipzig), 22, 679 (1970)] describe the substitution of methylamine for ammonia in the gasphase homocondensation of acrolein to produce lower overall yields and an increase of beta-picoline over pyridine, again using an amorphous catalyst.

Other references are also known wherein variations (intentional or not) in relative or total product yields are achieved over amorphous catalysts. For example, Minato et al. (U.S. Pat. No. 3,946,020) reacts acetaldehyde, formaldehyde and propionaldehyde (Example 2; Reference Example 2). An increased yield of beta-picoline is shown, the relative amounts of other alkylpyridines not being given. British Patent 929,694 also utilizes a reactant combination of formaldehyde, acetaldehyde and propionaldehyde to prepare pyridine and beta-picoline. British Patent 966,264 discusses the employment of formaldehyde with a lower aliphatic ketone and a saturated aliphatic aldehyde to prepare alkylpyridines. JP 61-53266 reacts acrolein, acetaldehyde and formaldehyde. Gamma-picoline yield is lowered without decreasing the yield of pyridine. JP 61-53265 prepares 3,5-lutidine and beta-picoline by reacting acrolein, propionaldehyde and formaldehyde. JP 45-39262 also employs a ternary mixture of reactants (acrolein, acetaldehyde and propionaldehyde) to prepare beta-picoline and pyridine, along with minimum production of gamma-picoline. British Patent 1,141,526 suggests that increasing the amount of acetaldehyde in a binary mixture of formaldehyde and acetaldehyde will decrease the yield of pyridine and beta-picoline while increasing the yield of alpha- and gamma-picoline.

While these references discuss, in an amorphous catalyst system, the effects on product composition of reactant changes, they do so only on a batch system basis and on small scale runs. They do not address the question of how to adjust product compositions on large scale continuous systems, and especially not on such systems employing zeolites as catalysts.

In fact, there is little discussion of useful techniques of varying the relative or total amounts of pyridine and alkylpyridines when a zeolitic catalyst is employed Feitler et al. (U.S. Pat. No. 4,675,410) discloses the use of a zeolite catalyst for the reaction and discusses various methods for improving overall yields and for varying the ratio of pyridine to alkylpyridines. These primarily involve use of a fluidized bed and temperature effects. The table in Column 4 of U.S. Pat. No. 4,675,410 does mention use of a ternary mixture in a reaction using a zeolite catalyst. However, no hint is given as to the expected product yields or any appropriate relative amount of the third component, butyraldehyde, in conjunction with the binary mixture, acetaldehyde and formaldehyde. Only the approximate underlying stoichiometry of the reaction is stated. EP 232,182 also involves the same basic system but requires thallium, lead or cobalt doping to optimize pyridine yield. Older references, e.g., U.S. Pat. No. 4,220,783 (inclusion of methanol or formaldehyde increases selectivity to pyridine) and U.S. Pat. No. 3,728,408, discuss more fundamental aspects of the basic reaction.

Thus, the need still exists for an improved method for varying the relative amounts of pyridine and alkylpyridines in zeolite-catalyzed reactions carried out continuously on large scales, without significantly decreasing overall yield of pyridine-type bases. Primarily, there is a need for increasing the relative amounts of alkylpyridines since most prior work has been directed to optimizing pyridine yields.

SUMMARY OF THE INVENTION

This invention involves a discovery that use of an appropriate third reactant in the binary zeolite-catalyzed reactions of the prior art will result in a surprisingly high total yield of pyridine and alkylpyridine(s). This high yield can be accompanied by an increase in the relative amount of alkylpyridines produced when the ternary component stoichiometrically produces an alkylpyridine. In essence, a skilled worker need merely select a third aldehyde or ketone which stoichiometrically will react with the binary mixture and ammonia to produce the desired alkylpyridine.

Thus, this invention provides, in a process for preparing pyridine, one or more alkylpyridines or a mixture thereof by reacting, continuously and on a large scale, a binary reactant mixture of carbonyl-containing compounds, each of which is an aldehyde or a ketone, with ammonia in contact with an effective amount of a zeolitic catalyst for the reaction to produce a total molar yield (binary yield) of pyridine and/or alkylpyridine(s), The improvement wherein a third aldehyde or ketone is added to said binary mixture without a break in reaction continuity, and the amount of said third aldehyde or ketone is selected whereby a ratio of reaction products is desirably adjusted and whereby the resultant total molar yield (ternary yield) of pyridine and/or alkylpyridine(s) remains high.

Thus, most significantly, this invention satisfies the need to continuously adjust the ratios and/or composition of products to adapt production schedules to the marketplace. By the simple addition of a product composition altering ternary component, without a resulting significant yield loss, a pyridine producer can now address market demands for increased $\beta$-picoline or make alternative products such as alpha picoline, 3-ethylpyridine, or 2,3-lutidine without building a new plant, completely switching feedstocks (i.e., acrolein+methyl ethyl ketone), completely switching catalysts (e.g., switching from the catalyst used in EP 232,182 to a thallium-free catalyst), or in any way disrupting ongoing operations.

This invention is especially surprising since it would be expected that use of ternary reactants would always produce lower total yields of pyridines and alkylpyridines than binary reactants. This is due to the statistical, increased likelihood of competing reactions caused by the presence of the additional reactant. This expectation is confirmed herein for amorphous catalysts (Comparative Example 1). For zeolite catalysts used in the past in this system, a similar yield loss would be expected by analogy. The extrapolatability of the amorphous catalyst yield loss to zeolitic systems would be expected to apply since the influence of shape selectivity factors in pentasil zeolitic catalysts in general would not be expected to impact on the yield of reactions where a ternary component is needed.

It has thus been discovered that, unexpectedly, adding an appropriate amount of a third component to the basic binary system is accompanied by either substantially no loss in total yield (pyridine+alkylpyridines) or a relatively minor loss in this total yield compared with the binary case. When relatively low additions of the third component are made, the yield in comparison to the binary mixture can be substantially the same. However, as the amount of third component is increased, the total yield will decrease to some extent. The appropriate amount for a given case can be determined routinely by a few orientation experiments. For example, in the reaction of Example 1, it has been observed that utilizing an amount of third component of 0.1 mole in a total of 3 moles (3.3%) will not affect the total yield. Increasing the amount of third component to 0.2 mole in a total of 3 moles (6.7%) results in a ternary yield about 93.5% of the binary yield. Thus, it may be preferred to limit the amount of ternary component to less than such amounts, e.g., up to about 5 mole%, 4 mole%, 3 mole%, 2 mole%, 1 mole%, etc.

The catalysts of this invention are crystalline aluminosilicate zeolites in the acidic form having a constraint index from about 1 to about 12. Preferably, these have an activity which is sufficient to produce a total average yield of pyridine and/or alkylpyridine(s) (as defined in Example 1) which is at least 80% under the conditions of Example 1 below. Comparative Example 2 demonstrates the effect of a lower catalyst activity on total yield, i.e., as the catalyst activity is lowered, the total yield falls more rapidly upon addition of a third component.

Preferably, the amount of the ternary component will be chosen so that the total yield of pyridine and alkylpyridines produced by the ternary mixture will be no less than 97% of the total yield of the binary mixture, most preferably no less than 98 or 99%, thereof or, most preferably, essentially the same or even higher than the binary yield.

In a preferred aspect of the process of this invention, the binary mixture will be acetaldehyde and formaldehyde. The preferred third component will be propionaldehyde to produce beta-picoline. Other third components/alkylpyridines include: acetone/2-methylpyridine, butyraldehyde/3-ethylpyridine, and methylethyl ketone/2,3-dimethylpyridine.

By "large scale" herein is meant a system on the scale of a pilot plant operation or larger, preferably a full-scale commercial production facility.

Without being bound by theory, it is felt that in the synthesis of pyridine bases, a certain amount of aldehyde or ketone is necessarily consumed to serve as a hydrogen acceptor. While hydrogen itself may not be a participant in the reaction, the loss of hydrogen is required for the aromatization of all pyridine bases wherein only three saturated aldehyde or ketone units are required to complete the ring. Inherently, formaldehyde is typically used commercially as such a hydrogen acceptor, i.e., it is used in excess, since it is the cheapest of the components. The resultant methanol produced is generally not detected, but rather dimethyl ether or more likely alkylamines are found [see, e.g., Levi et al., *Chemical Abstracts* 83, 58617m (1975)]. Thus, typically, approximately 2 moles of formaldehyde will be employed for every 2 moles of other saturated aldehydes used to form the pyridine ring with ammonia. One is used to participate in formation of the ring and the other to accept hydrogen so that the ring may become aromatic. It should be noted that in the synthesis of $\beta$-picoline from two acetaldehydes and two formaldehydes the hydrogen transfer does occur, but within the molecule. Thus, an excess amount of formaldehyde is preferably employed in U.S. Pat. No. 4,675,410. Of course, other aldehydes could also be utilized as hydrogen acceptors were this commercially feasible.

Using this theory, one can consider, in the prior art binary mixtures, one component to be a hydrogen absorber and the other to be merely a ring former. In this view, the preferred amount of the third component to be employed in this invention for purposes of optimizing the relative amount of the desired alkylpyridine can be defined as follows:

$$\frac{\text{hydrogen-absorbing component}}{\text{other component of binary mixture + ternary component}} \geq 1$$

Preferably, this ratio will have a value of 1–1.5, most preferably 1–1.2.

The principles described above with respect to saturated reactants also apply to mixtures wherein an unsaturated aldehyde or ketone is included. For example, the proper stoichiometry for the reaction of acrolein, propionaldehyde and formaldehyde to make beta picoline is 1/1/1. Substituting some methyl ethyl ketone for propionaldehyde proceeds by the same formula:

$$\frac{\text{hydrogen acceptor (formaldehyde)}}{\text{other saturated aldehydes and ketones (propionaldehyde + methyl ethyl ketone)}} \geq 1$$

The third component of this invention for use to form the reactant mixture can be a single aldehyde or ketone as mentioned above. However, the third component itself can be a mixture of two or more aldehydes and/or ketones as suggested above. The resultant increase in the alkylpyridine component of the product will vary correspondingly.

The foregoing discussion applies especially to the (acetaldehyde+propionaldehyde)+formaldehyde ternary mixture, but also applies analogously to the other ternary mixtures based on acetaldehyde and formaldehyde mentioned above. These details also provide valuable guidelines to a skilled worker employing any other ternary mixture based on a given binary mixture. Of course, this invention is not confined to the binary system of acetaldehyde+formaldehyde. It is applicable to binary systems in general. For example, the production of 3,5-lutidine from 2 propionaldehydes+2 formaldehydes could be modified by the substitution of methyl ethyl ketone for a portion of the propionaldehyde to give 2,3-lutidine, or by the substitution of some acetaldehyde to give $\beta$-picoline.

Thus, this invention in general is applicable to any combination of reactant carbonyl-containing which condense with ammonia to form pyridine and alkyl-substituted pyridines. Typically, these are $C_{2-5}$-aldehydes and $C_{3-5}$-ketones. These can be saturated or unsaturated. Formaldehyde is a preferred co-reactant. Except as otherwise noted herein, reaction conditions are fully conventional as discussed in Golunski et al., Kirk-Othmer, U.S. Pat. No. 4,675,410, and many others, all of whose disclosures are totally incorporated by reference herein.

For example, as is fully conventional, the carbonyl compounds may be used as monomers, dimers, trimers, other oligomers or polymers, e.g., solid polymers, etc. Water can also be included in the reactant stream. For example, formaldehyde can be added to the reaction medium in the form of formalin, the water content of which is non-critical. Any conveniently available formalin, e.g., 10% formaldehyde, 50% formaldehyde, 90% formaldehyde, etc., can be employed. Also usable are the paraformaldehydes, s-trioxane, paracetaldehyde, etc. Reactants can be of ordinary commercial purity.

Molar ratios of reactants will be determined in accordance with the foregoing. The total ratio of aldehydes and/or ketones to ammonia will be chosen in full accordance with the prior art. Only the relative amounts of the aldehydes and/or ketones per se will be significantly affected by the improvements of this invention. When water is included, the molar ratio of water to the non-hydrogen-absorbing component of the binary mixture (e.g., acetaldehyde in the binary mixture of acetaldehyde and formaldehyde) will generally be up to 10, i.e., generally 0–10, usually 0–3. The precise amount is essentially non-critical, unless unusual dilutions are involved.

The reaction can be conducted in the presence of normal industrial grade ammonia. The ammonia can be substantially contaminated with alkylamines. Alternatively, alkylamines can be positively introduced into the reaction system, e.g., via an ammonia recycle stream which often will include alkylamines in any event. This, of course, will have the usual beneficial economic and environmental effects. However, recycle of an alkylamine-containing ammonia stream (or adding alkylamines per se to the reaction system) can also be used as an adjunct means for controlling the ratio of pyridine to alkyl-substituted pyridines or the ratios among various alkyl-substituted pyridines. For example, increasing alkylamine concentration will produce a corresponding decrease in the ratio of pyridine to beta-picoline in the acetaldehyde/formaldehyde/ammonia or crotonaldehyde/formaldehyde/ammonia systems. Decreasing alkylamine concentration produces an increase in the ratio of pyridine to beta-picoline in these systems. Thus, deliberate addition of alkylamine or removal of alkylamine from the mentioned ammonia recycle stream can be employed. This additional degree of freedom in product control can also be used often to effect an overall yield increase of all the pyridine-type bases.

Where it is desired to remove alkylamines from a recycle stream, any conventional technique can be utilized, e.g., fractional distillation. For introduction of alkylamines into a feed stream, conventional techniques can similarly be utilized, e.g., any conventional metering means such as spray nozzles, etc. The concentration of alkylamine to be achieved in a given process will be determined by the desired yield and/or product ratio proportion desired. For any given combination of reactants, the amount of alkylamine required to achieve an obtainable desired product distribution will be readily determinable in conjunction with the guidance given in this specification and perhaps a few routine preliminary orientation experiments. The amount of alkylamine per se is not critical to the successful conduction of the reactions. Amounts from 0 to 100% of alkylamine (on a basis of amount of ammonia replaced thereby) can be employed. Typically, from 0–40% of the ammonia component in the feed stream will be provided by alkylamines, the remainder being ammonia per se. Primary, secondary and/or tertiary amines can be utilized, the precise chemical identity being uncritical. However, secondary and tertiary alkylamines are more efficient in affecting the product composition, i.e., lower amounts of secondary and tertiary amines are needed to achieve the same results as primary amines. In general, the alkylamines have from 1–18 carbon atoms in total, with any given alkyl group on a secondary or tertiary alkylamine typically having 1–6 carbon atoms. There is no strict limit on the molecular weight of the alkylamines as long as the desired effect is achieved. Typically, the alkylamines are saturated aliphatic compounds. Trimethyl and triethylamine are preferred, especially trimethylamine.

It is not necessary that alkylamines per se be added to the system or be removed therefrom. Alkylamine precursors serve the same function. That is, compounds in the system, which under the reaction conditions form alkylamines, will exert similar effects. Typically, the effect of a precursor will be equivalent to that exerted by an equivalent amount of the product alkylamine in the reaction system. Typical precursors are compounds which react with ammonia to form alkylamines, e.g., lower alkanols producing the mentioned primary, secondary or tertiary alkylamines under the reaction conditions, alkylthiols, alkylchlorides, etc. Also included are compounds with decompose under the reaction conditions to produce alkylamines, e.g., formamides, urea, etc. The amount of alkylamine precursor will correspond to that producing the alkylamine concentrations discussed above.

The process can be conducted either in a fixed bed or, preferably, in a fluidized or otherwise mobilized bed. Regarding the latter process, see especially U.S. Pat. No. 4,675,410. The processes are conducted in such beds using fully conventional considerations. For example, the throughput for the process of this invention when carried out in a fluidized bed will typically correspond to a weight hourly velocity in the range of 0.1–10, the optimum values being routinely determinable conventionally. Typically, the reaction is conducted at pressures of 0.1–100 atmospheres, generally 1–10 atmospheres, preferably at 1 atmosphere. Typical reaction temperatures are 300°–600° C., preferably 400°–500° C., and most preferably 420°–480° C.

Preferably, a catalyst to be used in the process of this invention will be a crystalline alumina-silicate zeolite in the acidic form having a constraint index from about 1 to about 12. Preferably, it is a member of the pentasil family of catalysts and will have a pore size greater than about 5.5 angstroms.

"Constraint index" is a conventional term of art which is defined, e.g., in Frillette et al., *Journal of Catalysis*, 67, 218–222 (1981). This parameter is fully sufficient to define those catalysts which will have a microstructure most suitable for use in the process of this invention, i.e., it defines those catalysts having pore characteristics such that the necessary constrained access to the interior of the catalyst is provided.

Constraint index (C.I.) values for some typical zeolites are given in the table below.

| Aluminosilicate | Constraint Index |
| --- | --- |
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Clinoptilolite | 3.4 |
| S-115 | ~1 |
| Beta | 0.6 |
| Zeolite Omega | 0.5 |
| H-Zeolon (mordenite) | 0.4 |
| REY | 0.4 |
| Amorphous Silica-Alumina | 0.6 |
| Erionite | 38. |

Catalysts having such constraint indices are readily commercially available. For example, the ZSM catalysts are available for rent from Mobil Oil Corporation, New York, N.Y., and are discussed in detail in U.S. Pat. Nos. 3,702,886 (ZSM-5); 3,709,979 (ZSM-11); 3,832,449 (ZSM-12); 4,016,245 (ZSM-35); and 4,046,859 (ZSM-38), as well as U.S. Pat. Nos. 3,894,106 and 3,894,107. Also satisfactory will be those ZSM catalysts discussed in U.S. Pat. No. 4,209,499 (ZSM-43); European Patent Application Publication No. 0023089A1 (ZSM-48); and U.S. Pat. No. 4,229,424 (catalyst having a structure intermediate between that of ZSM-5 and ZSM-11). Also suitable for use in the process of this invention will be the silica polymorph "silicalite" class of catalysts of Union Carbide Corporation, New York, N.Y., which have the properties required by this invention, e.g., as disclosed in U.S. Pat. No. 4,061,724, e.g., S-115.

In addition to the constraint index feature, it is also preferred that the crystalline aluminosilicate zeolite catalyst of this invention be in the acidic form. Herein, "acidic" is taken to mean that at least 10% of the catalytic sites which are available to hydrogen ions are in fact occupied by hydrogen ions, hydronium ions, or some other form of acidic species having Bronsted acidity. Preferably, 10–100% of such sites are occupied by hydrogen ions or other species, most preferably 80–100% since, generally, the higher the acidity, the higher will be the ratio of pyridine to beta-picoline at low temperatures. Catalysts having such acidities are readily commercially available, e.g., from the above-mentioned commercial sources. In any event, any zeolite otherwise meeting the requirements of this invention can be treated to achieve the preferred acidity by fully conventionally exchanging it, e.g., in the presence of an acid such as aqueous hydrogen chloride or NH$_4$Cl, etc., followed by conventional calcination in air at about 600°–800° C. for about 8 hours. See, e.g., Rajadhyaksha et al., J.Cat. 63, 510 (1980), and references cited therein.

Acidities as defined above can be fully conventionally determined, e.g., using the method described in Auroux et al., J.C.S. Faraday Trans. 1, vol II part II, 2544 (1979) and Vedrine et al., J.Cat. 59, 248 (1975).

Often, the various zeolites mentioned above or others will be prepared in the presence of organic cations and, hence, will be inappropriate for use in this invention, e.g., because they are catalytically inactive due to the presence of the organic cations. Presumably, this is caused by the occupation of the intracrystalline free space by such cations. These catalysts can be activated by conventional heating to higher temperatures in an inert atmosphere or vacuum, which is well known to result in the thermal destruction or removal of such organic cations. Moreover, it is often possible to convert natural zeolites to zeolitic catalysts which are suitable for use in this invention. This can be accomplished by various conventional activation procedures or other equivalent treatments, including base exchange, steaming, alumina extraction, calcination, combinations of the foregoing, etc. Natural minerals susceptible to such treatments include ferrierite, brewsterite, stilbit, dachiardite, epistilbite, heulandite and clinoptilolite.

All of the crystalline catalysts mentioned above will thus be useful for the process of this invention as long as they have a constraint index within the mentioned range and preferably an acidity within the mentioned range. In part these characteristics are those necessary for a catalyst which is capable of sustaining the conversion of a hydrocarbon such as methanol to gasoline or olefins.

The catalysts suitable for use in this invention are also understood to include not only crystalline aluminosilicate zeolite catalysts possessing x-ray crystallinity but also those possessing x-ray amorphism but possessing infrared crystallinity as defined and disclosed in Jacobs et al., J.C.S. Chem. Comm., 1981, 591–593. Similarly, the suitable catalysts are understood to include those in which various, usually trivalent, metals, e.g., boron, are apparently substituted for at least a portion of the aluminum in the crystal structure, e.g., boron, arsenic, antimony, vanadium, iron or chromium. Such catalysts include those disclosed in DOS Nos. 28 30 787, 28 30 830, 28 31 611, 28 31 630, 28 31 631 and 29 09 929. Such catalysts can even no longer contain aluminum. (DOS No. 28 30 787-examples 1-6, 12 and 13:100 mol% Al, examples 7-8:100 mol% B, example 9:100 mol% As, example 10:100 mol% Sb; DOS No. 28 31 611-example 1:75 mol% Fe, example 2:85 mol% Fe, example 3:90 mol% Fe; DOS No. 28 31 630-example 1:58 mol% Cr, example 2:72 mol% Cr, example 3:83 mol% Cr; DOS No. 28 31 631-example 1:65 mol% V; DOS No. 28 30 830-38 mol% As; DOS No. 29 09 929-75 mol% B). Preferably, the proportion of substitution by the trivalent metal will be less than 100%, typically less than 50%, preferably less than 10%.

Similarly, suitable catalysts will be understood to include those in which a tetravalent element is substituted for silicon in the crystal structure. As above, typically, the proportion of such a tetravalent substitution will be less than 100%, preferably less than 50%, most preferably less than 10%.

Preferably, the catalyst will be a member of the AlPO or SiAlPO families.

The catalysts suitable for use in the process of this invention will generally have $SiO_2/Al_2O_3$ ratios in the range of 12-1000, e.g., 12-700, more preferably 18-400, and most preferably 200-400, often about 350. Catalysts having such low amounts of aluminum are active for the process of this invention as long as the foregoing characteristics are met. The mentioned silica-to-alumina ratio can be fully conventionally determined using routine methods of analysis. See, e.g., Bibby et al., J. Catalysis, 72, 373-374 (1981). This ratio, as is fully conventional, refers, as closely as possible, to the ratio in the rigid crystalline framework of the zeolite crystal. The aluminum in the catalyst carrier or binder and in cationic or other form within the catalyst's channels is excluded, as is well known.

The necessary and sufficient characteristics of the catalyst of this invention are those disclosed herein. Thus, any conventional interpretations of the term "zeolite" which might be inconsistent or more limiting than the definitions given herein are not relevant.

Other catalyst-related characteristics and parameters will be conventionally determined, e.g., in conjunction with the details of the fixed or fluidized or otherwise movable bed which is being used and the details of this application. Such characteristics include the volume of the catalyst bed, the relative amount of catalyst, the contact time, the particle size (which will usually be in the range of 20-120 $\mu$m, preferably 45-100 $\mu$m), the particle shape (which will not be critical to the yields and ratios described above and includes powders, granules, molded products such as extrudates, crushed particles, etc.), etc.

Of course, since it is preferred that the process of this invention be carried out in a fluidized or otherwise movable bed, it is greatly preferred that the catalyst be used in the conventional form which is most suitable for such beds, e.g., in spray-dried form, having a preferred narrow particle size distribution of spherical particles; in conjunction with a fluidized diluent (e.g., 0-50 weight percent) which will increase the bed volume and, hence, the contact time; having a density and sufficient physical strength to be retained in the customary arrangements of catalyst recovery devices (e.g., cyclones); and sufficiently resistant to abrasion, erosion and attrition to achieve a long retention life in the system. One preferred form of catalyst is a microsphere incorporating binder and catalyst. The microsphere may be solid, hollow or amphora-like in structure. Technologies for preparation of such forms are conventional and are described, e.g., in A.G. Oblad, Oil & Gas Journal, 70 (13), 84 (1972), U.S. Pat. No. 3,450,680 and U.S. Pat. No. 3,140,249. The relative amounts of active catalyst and inert carrier or binder are not critical and can vary within a wide range, e.g., about 1-99% by weight of the carrier based upon the total weight of the combination. Usually, the amount of active catalyst is 5-80%, preferably 20-50% by weight of the composite.

Suitable such carrier or binder materials are fully conventional and include synthetic or naturally occurring substances as well as inorganic materials such as clay, silica and/or metal oxides. Suitable such substances are described, e.g., in U.S. Pat. No. 4,220,783, at Column 6, lines 12-45. Typically, the carrier will be a porous matrix, gel-like material such as alumina, silica-alumina, silica-magnesia, silica-zirconia, etc., as well as ternary such compositions including silica-alumina-thoria, silica-alumina-zirconia, silica-alumina-magnesia, silica-magnesia-zirconia, etc. The bound catalyst can also be extruded if desired. Binder and extrusion technologies are fully conventional.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius and, unless other indicated, all parts and percentages are by weight.

The entire text of all applications, patents and publications cited above and below are hereby incorporated by reference.

Each of the examples of this invention was conducted in a fluid bed reactor consisting of a stand pipe, a grid plate, and a two-inch diameter vertical stainless steel tube 36 inches long. The catalyst disengagement section consisted of a vertical segment 18 inches long flared, over 4 vertical inches, to 4 to 6 inches in diameter. This eliminated the need for a cyclone. The grid plate consisted of 2 $\mu$m stainless steel mesh. Organic feeds were introduced through a port 4 inches above the grid plate while ammonia was introduced beneath it. All reactants were heated to a temperature between 200° and 400° C. before introduction into the reactor. In the two-inch reactor, 1080 g of pentasil catalyst was typically used. The bed volume was 1900 cc. Products were condensed, using glass or metal water-cooled condensers, at intervals of 30 or 60 minutes for periods of 3-6 hours. Liquid products were analyzed by gas chromatography using propanol, butanol or 2,6-lutidine as an internal standard. The gas chromatographic analysis used a 60M fused silica Supelcowax(TM) capillary column, (0.32mm id., 0.50 $\mu$m film thickness).

EXAMPLE 1

Increased Beta-picoline Production Using Propionaldehyde as the Third Component 1080 g of a spray-dried catalyst formulation consisting of 40% of a catalyst (constraint index about 1; $SiO_2/Al_2O_3=350$; about 0.6 expanded bed density; spray-dried form), 40% Kaolin and 20% 85/15 amorphous silica-alumina was loaded into the two-inch fluid bed reactor. The catalyst was heated under a nitrogen flow of 60 l/hr to a temperature of 450° C. The nitrogen flow into the reactor was replaced with an ammonia flow at the rate of 111 g/hr. A mixture of acetaldehyde, 56% aqueous formaldehyde and propionaldehyde in the appropriate proportions was passed through a vaporizer (at 120° C.) into the reactor at a flow rate of approximately 400 cc/hr. The sample from the first 30 minutes of operation was discarded. Subsequent samples gave the results summarized below.

| Feed Composition Moles AcH/ Formaldehyde/ Prop. | | | Yield of Pyridine + Beta-Picoline at time into run (min) | | | | |
|---|---|---|---|---|---|---|---|
| | | | 15-60 | 60-120 | 120-180 | 180-240 | Avg.* |
| 1 | 2 | 0 | 0.8163 | 0.8324 | 0.8305 | 0.8277 | 0.8315 |
| 0.9 | 2 | 0.1 | 0.8153 | 0.8366 | 0.8304 | 0.8318 | 0.8335 |
| 0.8 | 2 | 0.2 | 0.7413 | 0.7785 | 0.7582 | 0.7502 | 0.7684 |
| 0.7 | 2 | 0.3 | 0.6352 | 0.6521 | 0.6769 | 0.6687 | 0.6645 |
| 0.5 | 2 | 0.5 | | | | | |

| Moles AcH/ Formaldehyde/ Prop. | | | Wt Ratio of Pyridine/Beta-Picoline at time into run (min) | | | | |
|---|---|---|---|---|---|---|---|
| | | | 15-60 | 60-120 | 120-180 | 180-240 | Avg. |
| 1 | 2 | 0 | 2.2534 | 2.2143 | 2.1744 | 2.2576 | 2.1944 |
| 0.9 | 2 | 0.1 | 1.3199 | 1.3039 | 1.3042 | 1.2670 | 1.3041 |
| 0.8 | 2 | 0.2 | 0.8201 | 0.8158 | 0.8022 | 0.8026 | 0.8090 |
| 0.7 | 2 | 0.3 | 0.5682 | 0.5590 | 0.5429 | 0.5372 | 0.5510 |
| 0.5 | 2 | 0.5 | | | | | |

*All averages in all examples are averages of the values of the 60-120 and 120-810 min. columns.

Retention of commercially acceptable high total yields has been verified upon addition of a propionaldehyde reactant stream to a continuous commercial plant producing pyridine and β-picoline by reaction of acetaldehyde and formaldehyde with ammonia.

COMPARATIVE EXAMPLE 1

Decreased Total Yield using Propionaldehyde as the Third Component and an Amorphous Catalyst The reaction was performed as in Example 1 except that Davison Catalyst 135 (a microspherical, amorphous silica/alumina (85/15) catalyst) was used (500 g) at 500° C. (conditions known to be preferred for this catalyst).

| Feed Composition Moles AcH/ Formaldehyde/ Prop. | | | Yield of Pyridine + Beta-Picoline at time into run (min) | | | | |
|---|---|---|---|---|---|---|---|
| | | | 15-60 | 60-120 | 120-180 | 180-240 | Avg.* |
| 1 | 2 | 0 | 0.5890 | 0.6440 | 0.6552 | 0.6530 | 0.6496 |
| 0.9 | 2 | 0.1 | 0.5833 | 0.6167 | 0.6154 | 0.6099 | 0.6161 |

| Moles AcH/ Formaldehyde/ Prop. | | | Wt Ratio of Pyridine/Beta-Picoline at time into run (min) | | | | |
|---|---|---|---|---|---|---|---|
| | | | 15-60 | 60-120 | 120-180 | 180-240 | Avg. |
| 1 | 2 | 0 | 1.6679 | 1.7235 | 1.7943 | 1.9277 | 1.7589 |
| 0.9 | 2 | 0.1 | 1.1552 | 1.1748 | 1.1949 | 1.2093 | 1.1849 |

COMPARATIVE EXAMPLE 2

Effect of Low Catalyst Activity on the Addition of a Third Component:

The procedure of Example 1 was repeated except that a lower activity version of the catalyst was used.

| Feed Composition Moles AcH/ Formaldehyde/ Prop. | | | Effect on Yield Time Into Run (min) | | | | |
|---|---|---|---|---|---|---|---|
| | | | 15-60 | 60-120 | 120-180 | 180-240 | Avg.* |
| 1 | 2 | 0 | 0.7652 | 0.7839 | 0.7347 | 0.6902 | 0.7593 |
| 0.9 | 2 | 0.1 | 0.7284 | 0.7270 | 0.6900 | 0.6414 | 0.7085 |

| Feed Composition Moles AcH/ Formaldehyde/ Prop. | | | Effect on Ratio of Pyridine/Beta-Picoline Time Into Run (min) | | | | |
|---|---|---|---|---|---|---|---|
| | | | 15-60 | 60-120 | 120-180 | 180-240 | Avg. |
| 1 | 2 | 0 | 2.7666 | 2.7274 | 2.7725 | 2.7105 | 2.7500 |
| 0.9 | 2 | 0.1 | 1.3747 | 1.3936 | 1.4008 | 1.3221 | 1.3972 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for preparing pyridine, one or more alkylpyridines or a mixture thereof by reacting, continuously and on a large scale, a binary reactant mixture of carbonyl-containing compounds, each of which is an aldehyde or a ketone, with ammonia in contact with an effective amount of a zeolitic catalyst for the reaction to produce a total molar yield (binary yield) of pyridine and/or alkylpyridine(s), said catalyst being a crystalline aluminosilicate zeolite in the acidic form having a constraint index from about 1 to about 12, the improvement wherein a third aldehyde or ketone is added to said binary mixture without a break in reaction continuity, the amount of said third aldehyde or ketone being from (a) an amount thereof whereby the resultant total molar yield (ternary yield) of pyridine and/or alkylpyridine(s) is substantially not decreased with respect to said binary yield, to (b) an amount thereof whereby the resultant ternary yield is about 97% of said binary yield and wherein in said binary mixture, one of said carbonyl-containing compounds is used in excess and serves as a hydrogen acceptor and wherein for said ternary mixture, the following molar ratio is maintained:

$$\frac{\text{hydrogen-absorbing component}}{\text{sum of other saturated carbonyl reactants}} \geq 1.$$

2. A process of claim 1, wherein said binary reactants are acetaldehyde and formaldehyde, said third reactant is propionaldehyde and β-picoline and pyridine are produced, with the yield of β-picoline being increased over that of the binary reaction.

3. A process of claim 1, wherein said binary reactants are acetaldehyde and formaldehyde, said third reactant is acetone and 2-methylpyridine and pyridine are produced.

4. A process of claim 1, wherein said binary reactants are acetaldehyde and formaldehyde, said third reactant is butyraldehyde and 3-ethylpyridine and pyridine are produced.

5. A process of claim 1, wherein said binary reactants are acetaldehyde and formaldehyde, said third reactant is methylethyl ketone and 2,3-dimethylpyridine and pyridine are produced.

6. A process of claim 1, wherein the amount of said third aldehyde or ketone is an amount whereby said ternary yield is no less than 98% of said binary yield.

7. A process of claim 1, wherein the amount of said third aldehyde or ketone is an amount whereby said ternary yield is no less than 99% of said binary yield.

8. A process of claim 2, wherein the molar ratio of reactants is:

$$\frac{\text{moles formaldehyde}}{\text{moles acetaldehyde + moles propionaldehyde}} \geq 1.$$

9. A process of claim 1, wherein the catalyst is a pentasil zeolite.

10. A process of claim 9, wherein the catalyst has substituted therein a tetravalent element for silicon in the crystal structure or trivalent element for aluminum in the catalyst structure.

11. A process of claim 1, wherein the ratio of $SiO_2$ to $Al_2O_3$ in the catalyst is about 12–1000.

12. A process of claim 1, wherein the ratio of $SiO_2$ to $Al_2O_3$ in the catalyst is about 200–400.

13. A process of claim 15, wherein the catalyst is in spray-dried form.

14. A process of claim 1, wherein the reaction is carried out in the presence of an alkylamine.

15. A process of claim 17, wherein the ammonia is supplied to the reaction in a form in which it is substantially contaminated with an alkylamine.

16. A process of claim 1, wherein the reaction mixture also contains an alkylamine precursor.

17. A process of claim 19, wherein the alkylamine precursor is methanol.

* * * * *